United States Patent
Mitsuhashi et al.

(10) Patent No.: US 7,285,199 B2
(45) Date of Patent: Oct. 23, 2007

(54) APPARATUS AND METHOD FOR ELECTROPHORETIC MICROSPOT CONCENTRATION

(75) Inventors: Masato Mitsuhashi, Irvine, CA (US);
Taku Murakami, Irvine, CA (US);
Tsuruki Tamura, Tsukuba (JP);
Masafumi Yohda, Tokyo (JP); Mina Okochi, Tokyo (JP)

(73) Assignees: Hitachi Chemical Research Center, Inc., Irvine, CA (US); Hitachi Chemical Co., Inc., Tokyo (JP)

( * ) Notice: Subject to any disclaimer, the term of this patent is extended or adjusted under 35 U.S.C. 154(b) by 687 days.

(21) Appl. No.: 10/399,882

(22) PCT Filed: Oct. 31, 2001

(86) PCT No.: PCT/US01/46035

§ 371 (c)(1),
(2), (4) Date: Sep. 10, 2003

(87) PCT Pub. No.: WO02/42500

PCT Pub. Date: May 30, 2002

(65) Prior Publication Data

US 2004/0069635 A1 Apr. 15, 2004

Related U.S. Application Data

(60) Provisional application No. 60/244,672, filed on Oct. 31, 2000.

(51) Int. Cl.
*G01N 27/447* (2006.01)
*G01N 27/453* (2006.01)

(52) U.S. Cl. ............ 204/450; 204/600; 204/465; 204/627; 204/543

(58) Field of Classification Search .......... 204/600, 204/601, 604, 450, 451, 456, 455, 627, 640, 204/543, 544

See application file for complete search history.

(56) References Cited

U.S. PATENT DOCUMENTS

| 4,139,346 A | 2/1979 | Rabbani |
| 4,159,933 A | 7/1979 | Allington et al. ........... 204/543 |
| 4,430,278 A * | 2/1984 | Jones, Sr. .................. 264/474 |

(Continued)

FOREIGN PATENT DOCUMENTS

DE 3715856 A1 12/1988

(Continued)

OTHER PUBLICATIONS

Derwent abstract of DE 03715856 A1 (publ. Dec. 1, 1988).*
Gribanov et al. (1996) "Use of aerosol A-300 amd GF/F (GF/C) filters for purifying fragments of DNA, plasmid DNA, and RNA" *Biokhimiia* 61:1064-70.

(Continued)

*Primary Examiner*—Alex Noguerola
(74) *Attorney, Agent, or Firm*—Knobbe, Martens, Olson & Bear LLP

(57) ABSTRACT

A method and apparatus for concentrating dilute biomolecules in samples using electrophoresis are described. The method involves using the charged nature of the biomolecules to localize them to a microspot containing a dialysis membrane. The method and apparatus may also be used for identifying the presence of a biomolecule in a mixture or to quantitate the amount of a specific biomolecule in a mixture. The method and apparatus may also be used to produce a high throughput method for analysis and quantitation of a sample containing biomolecules.

19 Claims, 6 Drawing Sheets

U.S. PATENT DOCUMENTS

| | | | |
|---|---|---|---|
| 4,906,561 A | | 3/1990 | Thornthwaite |
| 5,057,438 A | * | 10/1991 | Imai et al. .................. 436/516 |
| 5,158,661 A | * | 10/1992 | Hansen ....................... 204/607 |
| 5,340,449 A | | 8/1994 | Shukla ........................ 204/464 |
| 5,447,864 A | | 9/1995 | Raybuck et al. |
| 5,955,272 A | | 9/1999 | Lawrence et al. |
| 5,964,997 A | * | 10/1999 | McBride ..................... 204/451 |
| 5,990,298 A | | 11/1999 | Carmichael et al. |
| 6,113,763 A | * | 9/2000 | Henry et al. ................. 204/451 |
| 6,264,814 B1 | * | 7/2001 | Lange ......................... 204/450 |
| 6,287,440 B1 | * | 9/2001 | Arnold et al. ............... 204/450 |
| 6,319,379 B1 | * | 11/2001 | Davidson et al. ........... 204/453 |
| 6,432,290 B1 | * | 8/2002 | Harrison et al. ............ 204/453 |
| 6,495,319 B1 | | 12/2002 | McClelland et al. |
| 6,844,158 B1 | | 1/2005 | Mitsuhashi |
| 2002/0010323 A1 | | 1/2002 | Mitchell et al. |
| 2002/0039783 A1 | | 4/2002 | McMillan et al. |
| 2003/0152998 A1 | | 8/2003 | Mitsuhashi |
| 2004/0072193 A1 | | 4/2004 | Mitsuhashi |
| 2004/0265864 A1 | | 12/2004 | Mitsuhashi |

FOREIGN PATENT DOCUMENTS

| | | |
|---|---|---|
| DE | 03715856 A1 * | 12/1988 |
| EP | 0 776 700 A1 | 6/1997 |
| WO | WO 98/21321 | 5/1998 |
| WO | WO 99/32654 | 7/1999 |
| WO | WO 00/33050 | 6/2000 |

OTHER PUBLICATIONS retain. Thesaurus.com. Roget's New Millennium™ Thesaurus, First Edition (v 1.3.1), Lexico Publishing Group, LLC. http;://thesaurus.reference.com/search?q=retain (accessed: Sep. 19, 2006).

Matsuda, K. et al. (2001) "High throughput methodology for measurement of newly expressed poly(a) +mRNA from nuclei" FASEB J. 15:A515.

Joklik, W.K. (1981) "Procedures for studying transcription and translation of viral and host nucleic acids in interferon-treated cells" Methods in Enzymology 79:307-330.

Hamaguchi et al. (1998) "Direct reverse transcription-PCR on oligo(dT)-immobilized polypropylene microplates after capturing total mRNA from crude cell lysates" Clinical Chemistry 44:2256-2263.

Fukuchi et al. (1998) "DNA damage induces p21 protein expression by inhibiting ubiquitination in ML-1 cells" Biochemica et Biophysica Acta 1404:405-511.

Advanced Gene Computing Technologies Catalong (1997) "RiboCap High Throughput RT-PCR System", p. 6.

Mitsuhashi et al. (1992) "Gene manipulation on plastic plates" Nature 357:519-520.

Millipore Corporation (2001) Glass Fiber Filters Data Sheet, pp. 1-4.

Devary, Y. et al. (1991) "Rapid and preferential activation of the c-*jun* gene during the mammalian uv reponse" *Molecular and Cellular Biology*, pp. 2804-2811.

* cited by examiner ously.
APPARATUS AND METHOD FOR ELECTROPHORETIC MICROSPOT CONCENTRATION This is a U.S. National Phase under 35 U.S.C. §371 of International Application PCT/US01/46035, filed Oct. 31, 2001, which claims priority to US Provisional Application No. 60/244,672, filed Oct. 31, 2000, both of which are incorporated herein by reference in their entireties.

FIELD OF THE INVENTION

This invention relates to an apparatus and a method for the concentration of biomolecules onto a dialysis membrane for rapid, sensitive, and high throughput detection, characterization, and manipulation.

BACKGROUND OF THE INVENTION

Many technologies exist to detect and quantitate biomolecules, such as DNA, mRNA, proteins, small compounds, etc. However, available assays typically require expensive reagents and/or time consuming labor-intensive steps. For example, polymerase chain reaction (PCR) is a proprietary method which requires the use of an expensive enzyme such as Taq polymerase. Other methods such as chemiluminescence require enzymes and substrates. Methods using fluorescent probes require no enzymes, but are less sensitive than methods using enzymatic reactions.

Furthermore, sensitive assays are usually conducted in a small volume of less than 100 μL, so very small volumes of moderate to highly concentrated biomolecules are needed. Most purification methods result in large volumes of dilute samples which are not appropriate for sensitive assays. In addition, many molecular techniques require a series of enzymatic modifications with purification in between. This can result in continuous dilution and loss of the biomolecules, making the methods inefficient.

Thus, a simple, inexpensive method is needed for concentrating dilute samples of biomolecules, detecting the presence of small amounts of biomolecules in a sample, and analyzing the concentration of biomolecules in a sample. Preferably the method can be used for high-throughput applications.

Disclosed herein is the first systematic assay for sample concentration followed by detection, characterization, and manipulation, simultaneously.

SUMMARY OF THE INVENTION

In view of the above, an aspect of the present invention provides an apparatus for the concentration of biomolecules in a sample. In an embodiment, the apparatus comprises: (i) a first compartment for containing a first buffer to which a sample containing biomolecules is added; (ii) a second compartment for containing a second buffer including no sample; (iii) an insulation wall separating the first compartment and the second compartment, said insulation wall having a fine throughhole ("microspot"); (iv) a membrane covering the throughhole and blocking biomolecules contained in the sample from passing therethrough, wherein the first buffer and the second buffer are insulated by the insulation wall except for the throughhole covered with the membrane when the sample is loaded, wherein the first buffer and the second buffer are in electrical contact with each other via the membrane; (v) a first electrode provided in the first compartment to contact the first buffer when loaded; and (vi) a second electrode provide in the second compartment to contact the second buffer when loaded, wherein when a voltage is applied between the first and the second electrodes, biomolecules in the sample are subjected to electrophoresis and concentrated at the membrane-covered throughhole.

According to this embodiment, biomolecules in a sample can effectively be concentrated from the milli-litter level to the nano-litter level, for example. The level of concentration can be adjusted by adjusting the size of the throughhole, duration of operation, voltage difference, etc.

In the above, the first compartment has a compartment capacity and the throughhole has a throughhole capacity, wherein the ratio of the compartment capacity to the throughhole capacity may be in the range of $10^1$ to $10^{12}$, $10^1$ to $10^{10}$, or $10^2$ to $10^7$. In another embodiment, the ratio may be in the range of $10^1$ to $10^5$. The higher the ratio, the higher the level of concentration may become. Approximately 50%-80% of the first compartment may be filled with the first buffer in an embodiment.

In the above, the membrane may be a dialysis membrane. By selecting an appropriate dialysis membranes, it is possible to separate target biomolecules from other biomolecules having smaller molecular sizes than the target biomolecules.

The present invention may not be limited to but include the following various embodiments:

The isolation wall may be formed in a container having a top opening and a bottom having the throughhole, wherein the first compartment is provided inside the container, and the second compartment is provided outside the container.

The apparatus may further comprise an outer container in which the second compartment is formed.

The outer container may have a bottom which constitutes the second electrode. Further, the outer container may include a temperature controller to cool the outer container.

The membrane may be attached to the bottom of the container. This may be a backside of the bottom. The membrane may also be attached to the side of the container. The membrane may be attached to the bottom of the inner container by heat sealing, adhesives, or sonication.

The first electrode may be formed in a shape fitted inside the container. If the inner container is relatively small, the first electrode can be formed in a bar shape which may have a tapered end (or a triangular end) or a rectangular end.

The apparatus may further comprise an outer container in which the second compartment is formed.

The first electrode may be formed in a shape fitted inside the container.

The apparatus may comprise a plurality of the containers with the first electrodes.

The apparatus may comprise a plurality of the outer containers, wherein the containers are used as inner containers and fitted in the respective outer containers.

Each outer may container has a bottom which constitutes the second electrode.

The bottoms of the respective outer containers may be made of a common electrode plate functioning as the second electrode.

The inner and outer containers may be made of plastic and formed by injection molding.

The above embodiments can he adopted singly or in combination of any two or more.

Another aspect of the present invention provides an apparatus for the concentration and detection of biomolecules in a sample. In an embodiment, the apparatus comprises: (i) a first compartment for containing a first buffer to which a sample containing biomolecules is added; (ii) a second compartment for containing a second buffer including no sample; (iii) an insulation wall separating the first compartment and the second compartment, said insulation wall having a channel filled with a gel for electrophoresis, said channel covered with an insulation sheet except for one end spot (also "microspot") of the channel, said insulation wall having a hole underneath the end spot, said hole being covered with a membrane such as a dialysis membrane, wherein when the sample is loaded, the first buffer and the second buffer are insulated by the insulation wall except for a place where the end spot and the hole are located and the gel is present therebetween, wherein the first buffer and the second buffer are in electrical contact with each other via the gel; (iv) a first electrode provided in the first compartment to contact the first buffer when loaded; (v) a second electrode provide in the second compartment to contact the second buffer when loaded, wherein when a voltage is applied between the first and the second electrodes, biomolecules in the sample are subjected to electrophoresis and concentrated at the end spot; and (vi) a third electrode provided at another end of the channel opposite to the end spot, wherein a voltage is applied between the second electrode and the third electrode, biomolecules concentrated at the end spot are subjected to electrophoresis along the channel toward the third electrode.

According to this embodiment, not only concentration but also detection or secondary analysis can be conducted continuously. The aforesaid apparatus's configuration including the various embodiments can be adopted equally to this apparatus.

In the above, in an embodiment, the gel may be a linear gel. Further, the isolation wall may be shaped in a container having a top opening and a bottom plate having the channel, wherein the first compartment is provided inside the container, and the second compartment is provided outside the container.

In another aspect of the present invention, a method for the concentration of a biomolecule in a sample is provided. In an embodiment, the method comprises: (a) applying a sample to a first buffer, said first buffer being separated from a second buffer by an insulation wall having a fine throughhole, wherein a membrane covers the throughhole, said membrane being capable of blocking biomolecules contained in the sample from passing therethrough, wherein the first buffer and the second buffer are insulated by the insulation wall except for the throughhole covered with the membrane via which the first buffer and the second buffer are in electrical contact with each other; and (b) imposing a voltage difference between the first and the second buffers to subject biomolecules in the sample to electrophoresis, thereby concentrating the biomolecules at the membrane-covered throughhole. This method can be conducted by using any of the apparatus described above including the various embodiments.

In the above, the time effective to concentrate said biomolecules may be from about 1 min to about 1 day, suitably from about 10 min to about 3 hours.

In the above, the biomolecule may be selected from the group consisting of: DNA, rRNA, mRNA, tRNA, oligonucleotides, proteins, peptides, small molecules, lipids, steroids, microbes, and viruses.

For detection, the method may further comprise detecting the concentrated biomolecules, wherein said biomolecule is reacted with a detection moiety before concentration. The detection moiety may be selected from the group consisting of: a fluorescent dye, a fluorescent antibody, a fluorescent oligonucleotide, a colored marker, a dye, a radioactive label, and an intercalating agent. The detection moiety can be any type of substance having specificity to the target biomolecules, and in addition to the above, the moiety may include an antigen, hapten, biotin, avidin, ligand, receptor, binding proteins, transcription factors, drug, toxin, lectin, etc., depending on the type of biomolecules. Further, the detection moiety may be a substance which passes through the membrane, so that no washing is required before the concentration operation.

In the concentration step, the membrane may be selected to concentrate biomolecules having a larger molecular size than a predetermined size by molecular weight exclusion.

For quantification, the method may further comprise quantitation of biomolecules by monitoring the accumulation of biomolecules over a period of time; graphing the data; and determining the slope before the signal plateaus. The quantification can also be conducted by measuring a slope of a decrease in electric current between the first and second electrodes during electrophoresis, because the electric current decreases during electrophoresis because of the increase in electric resistance due to the accumulation of materials onto the dialysis membrane. If test samples contain a target molecule only in a very dilute form, this method may be effective.

Further, in an embodiment, the above method may further comprise a step of degassing the membrane or boiling the membrane prior to the concentration operation to reduce air or gas production during the concentration operation. Additionally, the voltage difference and the first and second buffers may be selected to reduce air or gas production during the concentration operation.

In other embodiments, the electric current may be selected to avoid bubble formation or prevent degradation/deformation/aggregation of the target biomolecules. Additionally, a pulsed electric current may be applied between the first and second electrodes to avoid bubble formation or prevent degradation/deformation/aggregation of the target biomolecules. Fur the same purpose, the method may further comprise cooling the second buffer during the concentration operation.

In still another aspect of the present invention, a method for the concentration and detection of a biomolecule in a sample is provided. In an embodiment, the method comprises: (a) applying a sample to a first buffer, said first buffer being separated from a second buffer by an insulation wall having a channel filled with a gel for electrophoresis, said channel covered with an insulation sheet except for one end spot of the channel, said insulation wall having a hole underneath the end spot, said hole being covered with a membrane, wherein the first buffer and the second buffer are insulated by the insulation wall except for a place where the end spot and the hole are located and the gel is present therebetween, wherein the first buffer and the second buffer are in electrical contact with each other via the gel; (b) imposing a voltage difference between the first and the second buffers to subject biomolecules in the sample to electrophoresis, thereby concentrating the biomolecules at the end spot; and (c) imposing a voltage difference between another end of the channel opposite to the end spot and the second buffer to subject the biomolecules concentrated at the end spot to electrophoresis along the channel toward the other end of the channel. This method can be conducted by using any of the apparatus described above having the secondary electrophoresis mechanism.

As with the aforesaid method, in the above method, the biomolecule may be selected from the group consisting of:

DNA, rRNA, mRNA, tRNA, oligonucleotides, proteins, peptides, small molecules, lipids, steroids, microbes, and viruses. Further, the method may further comprises detecting the concentrated biomolecules at the end spot, wherein said biomolecule is reacted with a detection moiety before concentration. Additionally, the detection moiety may be selected from the group consisting of: a fluorescent dye, a fluorescent antibody, a fluorescent oligonucleotide, a colored marker, a dye, a radioactive label, and an intercalating agent.

For purposes of summarizing the invention and the advantages achieved over the prior art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Further aspects, features and advantages of this invention will become apparent from the detailed description of the preferred embodiments which follow.

BRIEF DESCRIPTION OF THE DRAWINGS

These and other features of this invention will now be described with reference to the drawings of preferred embodiments which are intended to illustrate and not to limit the invention.

FIG. 6A is an angled view of the bottom portion.

DETAILED DESCRIPTION OF THE PREFERRED EMBODIMENT

Figure 1:
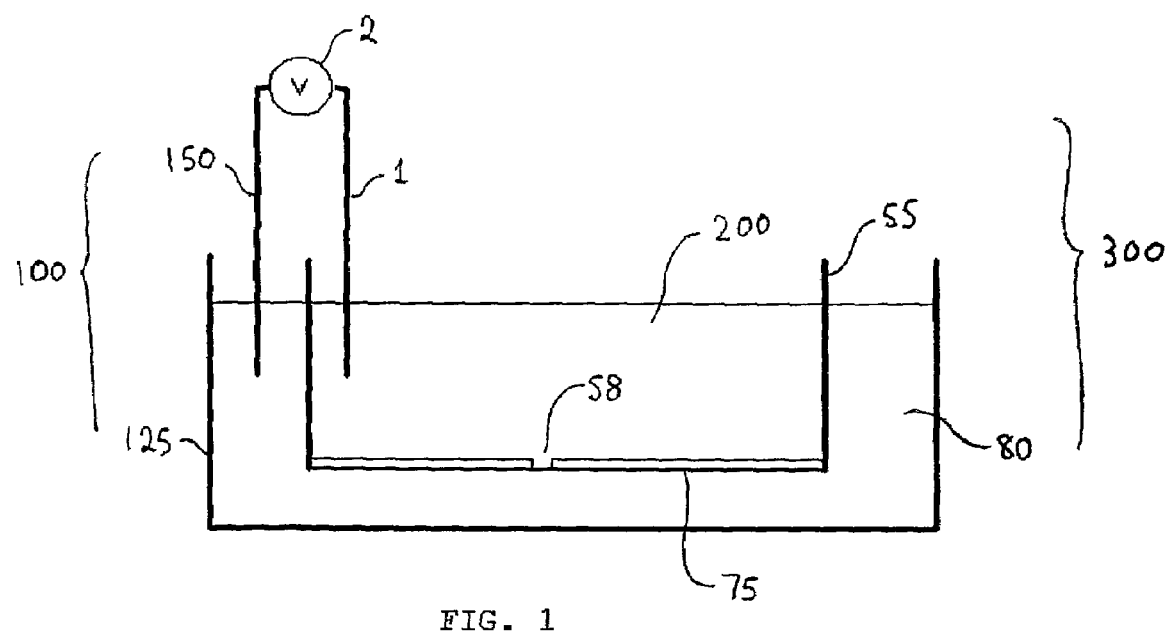
FIG. 1 is a schematic diagram showing an embodiment of an electrophoretic microspot concentration apparatus according to the present invention.

Nano technology, the detection or processing at nanoliter (nL) levels, is being applied in the field of biotechnology with greater frequency. However, the process is hindered by the need for using concentrated samples in very small volumes. Typically, samples are prepared for biotechnology at milliliter (mL) levels making them useless for most applications of nano technology. The process and apparatus herein provides a new interface between nL technology and mL technology, because it can be used for concentrating dilute biomolecules and further analyzing them, purifying them, or detecting the concentration of biomolecules.

In one embodiment the process for concentrating a dilute sample is as follows: a dialysis membrane is attached to the bottom of a first container containing a sample in a volume of one or more mLs. The bottom of the container has a sample collector which consists of a small hole or "microspot" with a dialysis membrane. The first container is immersed into a solution or buffer contained in a second container. An electrode is inserted in each container, and a voltage is applied between the first container and the second container, thereby conducting electrophoresis. The dialysis membrane passes electricity, and the sample moves toward the dialysis membrane. The sample or biomolecule cannot pass through the dialysis membrane, and thus the sample is concentrated at the microspot. By adjusting the size of the microspot, the degree of concentration can be adjusted. When a fluorescent or some other type of marker is coupled with the sample, quantification can be performed during the concentration process. Further, if the microspot is connected to a micro channel, secondary electrophoresis can be conducted along the micro channel upon completion of concentration at the microspot. This allows for a very fine sample analysis, because during the process, the sample is concentrated and because little is lost between concentration and analysis.

As described above, this method allows not only concentration of the sample, but also allows a highly sensitive quantification and secondary electrophoresis. Thus this method is very useful as an interface for nano technology, the next generation of biotechnology.

In an alternative embodiment, the first container and the second container can be placed side by side, separated by a wall having a microspot where a dialysis membrane is attached.

The size of the inner container (defining the first compartment filled with a buffer including a sample and having a microspot at the bottom) and the size of the microspot depend on the amount of concentration that is needed for the sample to be useful for the next step or to be readable by a fluorescent or other detection method. In an embodiment, the ratio of the capacity of the first container to the capacity of the microspot may be approximately $10^1$ to $10^{12}$, $10^1$ to $10^{10}$, or $10^2$ to $10^7$, and in other embodiments, approximately $10^1$ to $10^5$ or $10^1$ to $10^3$. The ratio may directly contribute to the level of concentration. The higher the ratio, the higher the level of concentration may become.

For example, in an embodiment, a microspot having a diameter of approximately 20 µm can be formed in a plate having a thickness of approximately 0.3 mm by injection molding. In this case, the capacity of the microspot is approximately 0.12 nL (0.02×0.02×0.3=0.12). Although biomolecules accumulate on a membrane, the thickness of the accumulating layer on the membrane may be much lower than the depth of the microspot. For example, if the thickness of the accumulating layer ranges from 0.3 µm to 3 µm (i.e., 1/100-1/1,000 of the depth of the microspot), the depth of the microspot which is required for that accumulation will be 0.3-3 µm. Thus, the required capacity of the microspot will be 0.12-1.2 pL. If the first container has a capacity of 2 mL, the ratio of the capacity of the container to the capacity of the microspot will be the $10^9$ order to the $10^{10}$ order. If the capacity of the container is higher than the above, the ratio will be higher than the above. Because the size of the container and the microspot can be scaled up or down easily, the ratio can vary and be selected according to the concentration theme, technical preferences, and technical limitations. The size of the microspot may range from the nano— or pico-litter order to the milli-litter order.

For example, the size may range from approximately 1 nL to 1 mL, from 0.1 L to 100 L, from 1 nL to 10 L, or from 0.1 L to 1 L in capacity in embodiments, and this can be scaled up and down. As with the capacity, the diameter and depth of the microspot may be selected according to the concentration theme, technical preferences, and technical limitations. For example, the diameter may range from approximately 0.01 mm to 30 mm, form 0.1 mm to 10 mm, or from 0.1 mm to 5 mm in embodiments, and the depth of the microspot may range from approximately 0.01 mm to 20 mm, from 0.1 mm to 10 mm, or from 0.1 mm to 1.0 mm in embodiments.

In the above, in an embodiment, approximately 50-80% (30-100% in some case) of the capacity of the inner container may correspond to the volume of the first buffer.

Any dialysis membrane which is appropriate with a biomolecule sample may be used. Preferably, the dialysis membrane has a constant molecular weight cut-off. Many types and brands of dialysis membrane are available to one of skill in the art. For example, flat sheet dialysis membranes (Spectra/Por®, Spectrum laboratories, Rancho Dominguez, Calif.) are available as a 3 mm diameter disc, a 47 mm diameter disc, a 100 mm diameter disc, or a rectangle. The MW exclusions available include: 100 d, 500 d, 1 kD, 2 kD, 3.5 kD, 6 kD, 8 kD, 10 kD, 15 kD, 25 kD, 50 kD, 100 kD, and 300 kD. The Biotech dialysis membranes are made by a process that eliminates the use of metal salts in manufacturing, making them more suitable for concentrating biomolecules which will be reused. In one embodiment, a Spectra/Por Type: 1 MWC0:6-8000, flat width 32 mm, diameter 20.4 mm, vol/length 3.3 mL/cm, length 30 m/100 ft, reorder No. 132655 may be used. Alternatively, heat-stable dialysis membrane, Spectra/Por Type F with a molecular eight cut off of 80K may be used.

The thickness of the dialysis membrane used in the method depends on the purpose for the sample, whether t will be detected on the membrane and how it will be detected. It also depends on the volume and concentration of DNA or protein in the solution. The smaller the diameter, the more sensitive the assay which can be developed. However, the dynamic range becomes low. If the DNA or protein has migrated into the inside of a thick membrane, detection may not work as well because of the interference with the excitation and emission light. If the target molecules stay on the top of the membrane, the thickness will not matter as long as the detection light (particularly if it is fluorescent) is collecting from the top. Transparency of the membrane is important, however, if the light is measuring from the bottom. Thus, the thickness of the membrane is that of those dialysis membranes which are obtainable as a commercial product (for example from Spectra/Por). Alternatively, the dialysis membrane may have a thickness ranging from approximately 0.001 mm to 10 mm, from 0.01 mm to 1 mm, or from 0.1 mm to 0.5 mm in embodiments.

As with the microspot, the capacity and the shape of the first container may be selected according to the concentration theme, technical preferences, and the technical limitations. For example, the capacity of the fist container may range from approximately 0.1-500 mL (or approximately 0.1-10 mLs) in an embodiment.

The capacity and shape of the second container may not affect the concentration theme and may be selected according to technical preferences and technical limitations. For example, the second container may have a capacity of from approximately 0.1-100 mLs in an embodiment, which also depends on the capacity and the shape of the first container.

Any type of container can be used for the first and second containers as long as they can store a solution used for electrophoresis. For example, the container may be a typical 6 well plates or 35 mm tissue culture dishes which are made of materials such as polystyrene. Alternatively, the container may be made of some other type of strong polyer. For example, 96 well plates, 384 well plates or larger may be used for the presently claimed invention. Preferably, the container is made of a material that has a high heat stability as well as a low absorption. The material should be rigid enough that a small hole can be fashioned for the microspot. Polypropylene is used for one embodiment, however, polypropylene is not rigid and difficult to fashion a stable small hole in. Other materials which might be used include, but are not limited to, polystyrene, heat stable polystyrene, and cyclo olefin polymers.

A usable solution or buffer contained in the first container (typically the cathode buffer) for dissolving a biological sample works best if it has a small transport number and does not interfere with DNA, RNA, and protein, depending on the biological molecule which is to be concentrated. Buffers which may be used include those listed in Good's buffer et al. In 1966, Good, et al. (Good, N. E. et al. 1966 Biochemistry 5, 467) introduced a series of new biological buffers for use in the physiological pH range. These buffers are particularly useful for biological molecules. Thus, any buffers identified in the Good reference are useful and other buffers, including, but not limited to: Tris EDTA solutions, HEPES (2-[4-(2-Hydroxyethyl)-1-piperazinyl]ethanesulfonic acid), MOPS (3-Morpholinopropanesulfonic acid), Bis-Tris (Bis(2-hydroxyethyl)iminotris(hydroxymethyl)methane), ADA (N-(2-Acetamido)iminodiacetic acid), PIPES (Piperazine-1,4-bis(2-ethanesulfonic acid)), ACES (N-(2-Acetamido)-2-aminoethanesulfonic acid), MOPSO (2-Hydroxy-3-morpholinopropanesulfonic acid), BES (N,N-Bis(2-hydroxyethyl)-2-aminoethanesulfonic acid), TES (N-Tris(hydroxymethyl)methyl-2-aminoethanesulfonic acid), DIPSO (3-[N,N-Bis(2-hydroxyethyl)amino]-2-hydroxypropanesulfonic acid), TAPSO (2-Hydroxy-N-tris(hydroxymethyl)methyl-3-aminopropanesulfonic acid), POPSO (Piperazine-1,4-bis(2-hydroxy-3-propanesulfonic acid), dihydrate), HEPPSO (4-(2-Hydroxyethyl)piperazine-1(2-hydroxypropanesulfonic acid) monohydrate), EPPS (3-[4-(2-Hydroxyethyl)-1-piperazinyl]propanesulfonic acid), Tricine (N-[Tris(hydroxymethyl)methyl]glycine), Bicine (N,N-Bis(2-hydroxyethyl)glycine), TAPS (N-Tris(hydroxymethyl)methyl-3-aminopropanesulfonic acid), CHES (2-(N-Cyclohexylamino)ethanesulfonic acid), CAPSO (N-Cyclohexyl-2-hydroxy-3-aminopropanesulfonic acid), CAPS (N-Cyclohexyl-3-aminopropanesulfonic acid), and MES (2-Morpholinoethanesulfonic acid, monohydrate). For a serum sample, the barbitol buffer (5,5-Diethylbarbituric acid) may be preferred.

A usable solution or buffer contained in the second container (typically the anode buffer) for conducting electrophoresis includes, but is not limited to 1×TBE, TAE, and includes those buffers listed for the first container.

The voltage applied between the electrodes inserted in the first and second containers, respectively, may be selected according to the configuration of the apparatus, e.g., the size of the first container, the size of the microspot, the concentration theme (electrophoretic characteristics of target biomolecules, target concentration, etc.), the size of the second container, etc. For example, the voltage difference may range from approximately 5 mV to 500 V in an embodiment, 5 V to 150 V in another embodiment. The current used may range from approximately 1 µA to 1 A in an embodiment, from 0.01 mA to 30 mA, or from 1 mA to 10 mA in embodiments.

Electrodes usable for the apparatus herein may be made of materials including, but not limited to: Pt, Au, carbon electrodes (including pyrolytic graphite, glassy carbon, carbon paste, etc.) for the anode electrode. For many applications, Pt would be the most suitable. Materials which may be used for the cathode include, but are not limited to: Pt, Au, Pd, Ag, Cu, Fe, Ti, and carbon electrodes. The negative electrode and the positive electrode may be made of the same material or may be made of different materials.

Methods for reducing air or gas production are also envisioned for the method and apparatus. Such methods include but are not limited to: degassing the dialysis tubing, boiling the dialysis tubing, selecting the appropriate voltage and buffer. A cooling system may also be used to (I) avoid bubble formation, and (II) prevent degradation/deformation/aggregation of the target molecules. This can be achieved by a variety of techniques, including but not limited to (I) reducing electric current, (II) applying a pulsed electric current, and (III) mixing the buffer in the lower plate with a cooling system. It is envisioned that mixing the buffer in the upper plate with a cooling system is not applicable, because the mixing process would dilute the accumulated sample at the microspot.

Dyes may be used as markers of electrophoresis to tell when the process is over and the biomolecule is concentrated in the microspot. Dyes which may be used for marking electrophoresis include, but are not limited to: methyl red, Coomassie Brilliant Blue G (Molecular Formula: C47H48N307S2Na; CAS: 6104-58-1), Coomassie Brilliant Blue R 250 (Molecular Formula: C45H44N307S2Na; CAS: 6104-59-2), Sypro™ Orange, Sypro™ Red, Sypro™ methyl red, Yoyo™-1 (quinolinium, 1,1'-[1,3-propanediylbis[(dimethylimino)-3,1-propanediyl]]bis[4-[3-methyl-2-(3H)-benzoxazolylidene)mehyl]]-,tetraiodie), Toto™-1 (quinolinium,1-1'-[1,3-propanediylbis[(dimethyliminio)-3,1-propanediyl]]bis[4-[(3-methyl-2 (3H)-benzothiazolylidene)methyl]]-,tetraiodide), Toto™-3, RiboGree™, SyberGold™, PicoGreen™, YoPro™-1 (quinolinium,4-[3-methyl-2(3H)-benzoxazolylidene)methyl]-1-[3-(trimehylammonio)propyl]-,diiodide), and SyberGreen™.

For quantitation of DNA methods such as reading DNA absorbance at 260 nm, staining DNA with dyes (and comparing to standards), Ethidium bromide intercalation, and staining DNA with fluorescent dyes have been used. Ethidium Bromide provides a sensitivity for dsDNA detection better than UV. However, to detect DNA in solution at very low concentrations, fluorescent dyes have become the method of choice. Some of the newly developed fluorescent dyes include unsymmetrical cyanine dyes of three types: monomer dyes with cationic side chains, dimers of these dyes, and substituted monomers. Fluorescent dyes which can be used include, but are not limited to: Hoechst®332589, YoPro™-1 and Yoyo™-1, PicoGreen™ and OliGreen™, Molecular Probes), and SyberGreen I and II (Applied Biosystems). The PicoGreen™ dye binds dsDNA specifically and the resulting signal is not affected by existing ssDNA and RNA in solution. OliGreen™ is a ssONA specific dye which is an ultrasensitive fluorescent nucleic acid stain for quantitating oligonucleotides and ssDNA in solution. The OliGreen™ reagent exhibits a large fluorescence enhancement upon binding to ssDNA, however, the OliGreen™ dye is somewhat less selective for ssDNA than the PicoGreen™ dye is for dsDNA. Each of the fluorescent dyes have specific uses and may be more useful depending on the type of molecule which is being quantitated and whether the molecule will be used subsequently. However, OliGreen™ has been used to detect oligonucleotides in complex mixtures, such as blood or serum, with good sensitivity before or after extraction of the serum with phenol and chloroform.

Biological samples or biomolecules which can be used herein are any biomolecules which are charged. Preferably, the biomolecules are large enough to be retained on a dialysis membrane. Because dialysis membranes can be purchased or made with an almost limitless choice of pore (molecular weight retention or exclusion) sizes, it is envisioned that almost any type of biomolecule can be used with the method and apparatus herein. Biological samples or biomolecules which can be used with the method and apparatus herein include, but are not limited to: proteins, peptides, microorganisms (prions, viroids, viruses, bacteria, fungi, protozoa), cellular organelles or structures (ribosomes, polar bodies, membranes), carbohydrates, sugars, lipids, nucleic acids (RNA, DNA, mRNA, tRNA, rRNA), phospholipids, steroids, fatty acids, pharmaceuticals or small molecules, and glycoproteins. The biomolecule may be tagged or labeled, and the tagging or labeling may or may not produce a charged molecule. Labels which may be used include, but are not limited to: radioactive moieties, radioactive probes, or radioactive antibodies, dyes, fluorescent moieties, fluorescent probes, or fluorescent antibodies, colored moieties, colored antibodies or parts thereof, DNA intercalators, peptides, ligands, and small molecules. The labels may be specific for the biomolecule to be detected, such as specific antibodies or nucleic acid probes, or alternatively, the labels may be nonspecific, such as DNA intercalators or dyes. The labels may make the biomolecules visible or the labels may make the biomolecules insoluble or retainable by the dialysis membrane.

The initial concentration of the sample varies depending on the biomolecule used, but may be in the range of from approximately $10^3$ molecules/10 mLs to $10^7$ molecules/10 mLs. Preferably, the concentration is from approximately $10^4$ molecules/10 mLs to $10^6$ molecules/1 mL.

The microchannel which can be used for secondary electrophoresis may have a width of from about 10 µm to about 100 µm, preferably from about 10 µm to 50 µm, and a depth of from about 10 µto 100 µm. The channel has a length sufficient to separate a target biomolecule by electrophoresis, e.g., 30-100 mm. The channel may be formed in a straight line, a meandering line or a whirlpool. A microspot may be formed at an end of the micro channel by, for example, covering the remaining portion of the micro channel with a plastic film.

The microchannel chip may be made of plastic such as acrylic resin by injection molding, for example. However, the chip can be made of glass.

A gel for secondary electrophoresis contained in the microchannel may include polyacrylamide, agarose and variants thereof. The gel may be a separation buffer containing a sieving polymer, e.g., a crosslinked polymer or a liner polymer, in an amount effective to conduct migration of the target biomoleclues. The liner polymer is preferred and includes an alkylcellulose derivative, for example, which is preferably selected from the group consisting of hydroxyethylcellulose, hydroxypropylmethylcellulose, hydroxypropylcellulose, and mehylcellulose, in an amount of, e.g., 0.1-2% by weight in the gel. Without the sieving gel, some materials may be separated for detection. However, for detection of DNA or RNA, the sieving gel may be required because DNA and RNA have the same electric charge and molecular type even if the molecular sizes are different.

When conducting the secondary electrophoresis, a third electrode is used and activated. The third electrode is placed at the other end of the micro channel, so that electrophoresis can be carried out in the micro channel toward the other end, wherein the second electrode may be used upon switching from the negative to the positive.

The voltage difference applied for the secondary electrophoresis may be in the range of from about 100-1,000V, preferably about 300-500V.

The secondary electrophoresis may be completed in a time from about 1 min to about 3 days. Typically, electrophoresis is completed in from about 5 min to about 1 day, including 10 min, 20 min, 30 min, 40 min, 50 min, 60 min, 1.5 hours, 2 hours, 3 hours, 4 hours, 5 hours, 6 hours, 7 hours, 8 hours, 9 hours, 10 hours 11 hours, 12 hours and 18 hours. For example, by conducting the secondary electrophoresis, degradation of RNA can be detected by detecting bands of rRNA. Alternatively, the size of transcripts or proteins can be analyzed.

The method and apparatus may be used for many applications which involve biomolecules, including, but not limited to: cloning; quantitating levels of transcription products, quantitating translation products, quantitating specific proteins, and other biomolecules in a cell or tissue; identifying the presence of a biomolecule in a cell or tissue; labeling types of proteins, such as phosphoproteins with antibodies to analyze the numbers, types or amounts of such proteins in a cell or tissue; concentrating RNA transcripts, cDNA, or protein which has been isolated from a cell or tissue; identifying the presence of a single nucleotide polymorphism in a patient sample; diagnosis of disease by the expression of a gene or mutation; quantitating the amount or type of proteins in a biological fluid; identifying the presence of a pathogen in a biological fluid or sample; identifying a ligand in a pool of proteins; identifying a molecule which interacts with a protein or other biomolecule in a pool of such molecules; and identifying the presence of antibodies which recognize a pathogen or a specific antigen in a pool of proteins or a patient sample. However, one of skill in the art may recognize other such applications for the technology disclosed herein.

The Apparatus for Electrophoretic Microspot Concentration (EMC)

With reference to FIG. 1, the apparatus for Electrophoretic Microspot Concentration (EMC) 300 is composed of an Upper Electrode Plate (UEP) 1, a Sample Concentration Plate (SCP) 55, and a Lower Electrode Plate (LEP) 100. The UEP may be a part of the plate or it may be a separate electrode as in FIG. 1. The Upper electrode 1 is inserted into the sample container 55, into the sample, which may be diluted in an appropriate buffer 200. The sample container 55 is placed into a second container 125 which may be part of the Lower Electrode Plate (LEP) 100 or may be attached to the lower electrode 150. In FIG. 1, the Lower electrode 150 is placed into the electrophoresis buffer 80 which is within the lower electrophoresis buffer container 125. A dialysis membrane 75 is attached to the bottom of the sample container 55 which contains a hole 58. When an appropriate voltage is applied 2, the biomolecules move toward the lower electrode 150 through the hole (sample container) 58 and end up bound to the dialysis membrane 75.

If a dye or a tracer was added to the sample, the biomolecules may then be analyzed for the presence or concentration of a specific biomolecule. Alternatively, the biomolecules may be removed from the dialysis membrane by any means known to one of skill in the art. For example, a pipettor may be used to remove the biomolecules. The biomolecules may then be subjected to further analysis or enzymatic treatment. Alternatively the biomolecules may then be used to produce a microarray or a DNA chip. The biomolecules may be cloned or sequenced. However, it is envisioned that the biomolecules may be used for any method known to one of skill in the art.

Figure 2:
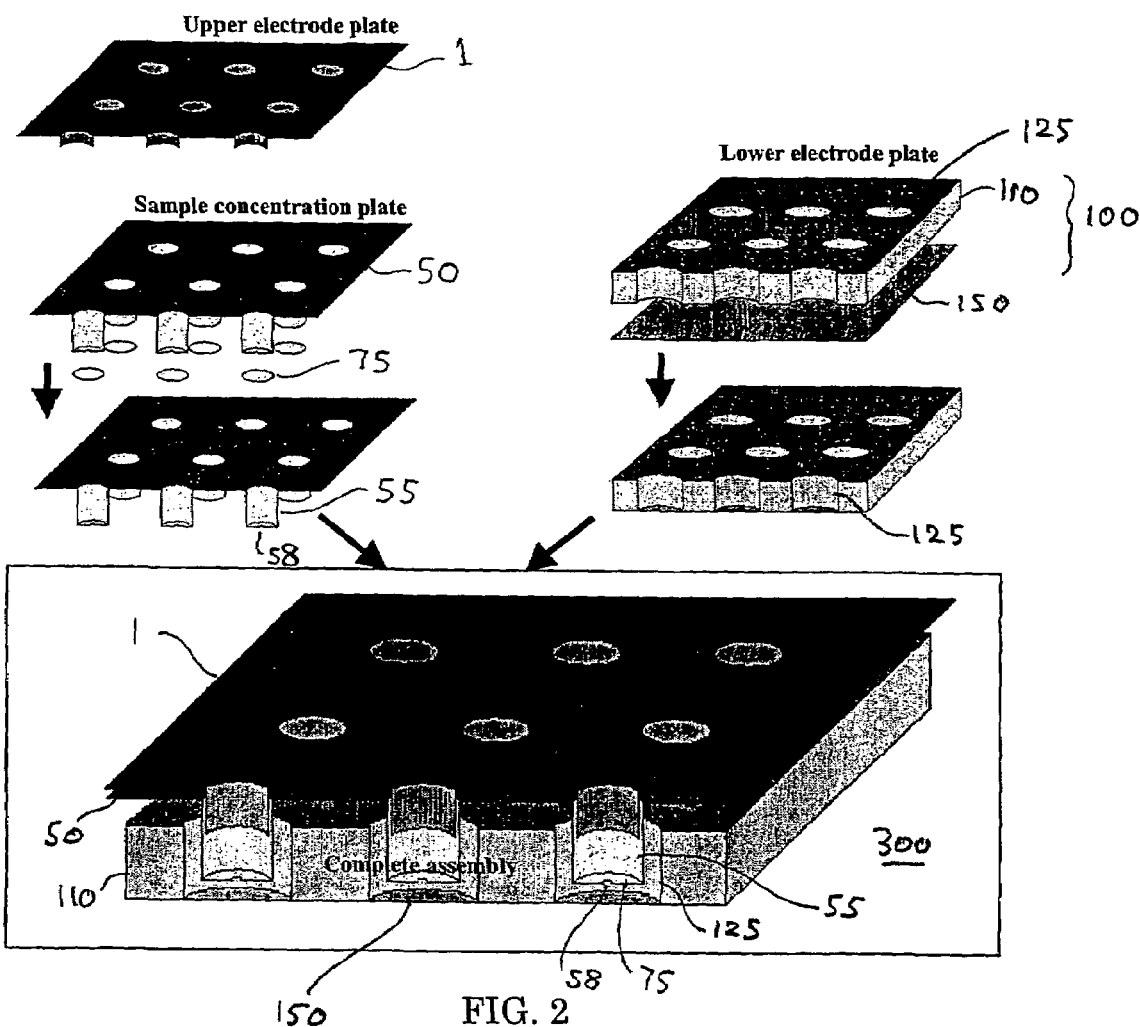
FIG. 2 is a schematic diagram showing structures of an electrophoretic microspot concentration apparatus comprising three components according to an embodiment of the present invention.

In a further embodiment, the apparatus for Electrophoretic Microspot Concentration is configured as in FIG. 2. The apparatus for Electrophoretic Microspot Concentration (EMC) 300 shown in FIG. 2 has three basic components: an Upper Electrode Plate (UEP) 1, a Sample Concentration Plate (SCP) 50, and a Lower Electrode Plate (LEP) 100 (FIG. 2). The LEP 100 is a microplate 110 with a single sheet electrode typically on the bottom 150 (FIG. 2).

When in use, electrophoresis buffer is added into the second container 125 of the LEP and the first container 58 of the SCP 50 is placed into the second container 125 of the LEP 100 (FIG. 2). The SCP 50 has a plastic bottom with a small hole in the center 58 (the sample collector), and a dialysis membrane 55 is also attached to the bottom.

Figure 3:
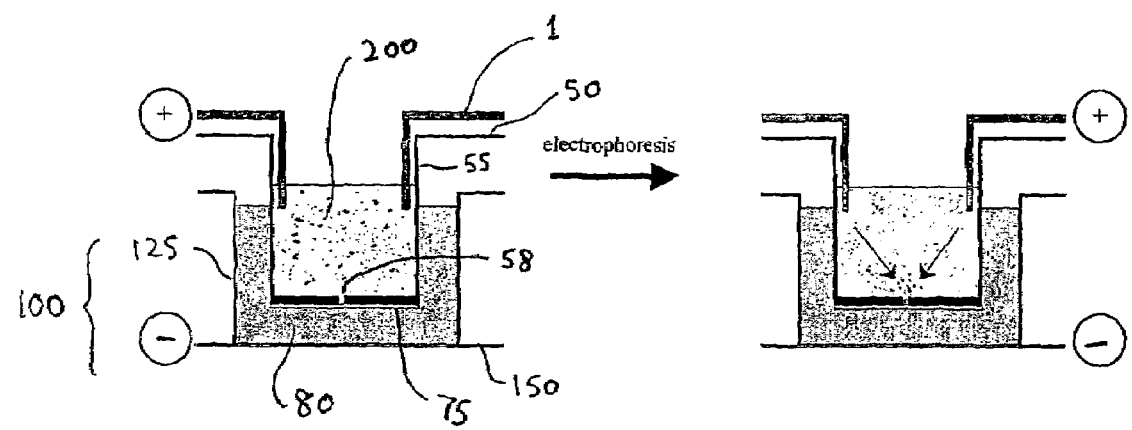
FIG. 3 is a schematic diagram showing the principle of electrophoretic microspot concentration using the apparatus shown in FIG. 2.

FIG. 3 is schematic cross sectional view showing an embodiment of the Electrophoretic Microspot Concentration (EMC) assembly 300. This figure shows the principle of EMC using the assembly 300. In FIG. 3, the Upper Electrode 1 which is placed on top of the first container 55 of the Sample Concentration Plate (SCP) 50. The Lower Electrode Plate (LEP) 100 is composed of a second container 125 with a bottom electrode 150. The LEP 100 has a second container 125 as part of the structure or attached to it. Electrophoresis buffer 80 is added to the second container 125. Diluted samples 200 are re-suspended in electropholesis buffer and added to the first container 55 in or on the SCP 50. Then, the UEP 1 is placed on top of the SCP 50, where the upper electrode is submerged into a sample solution 200.

Once the appropriate power of electricity is applied in the appropriate direction to both the upper 1 and lower electrode 150, charged biomolecules migrate into the sample collector 58 (the small hole) at the bottom of the SCP 50. During electrophoresis, the biomolecules will stay on the top of the dialysis membrane 75, whereas small ions move freely between the SCP 50 and the LEP 100.

If the target biomolecules are stained with a specific dye or a probe, the sample concentration can be very sensitively detected by, e.g., fluorometric detection based on concentrated signals. For example, if one mL of diluted sample is applied to the SCP, and the size of the sample collector is 1 mm×1 mm×1 mm, the sample will be concentrated 1000 fold. Thus, variations in the size of the sample container and the sample collector can allow for a variety of concentrations.

One application of this technology is for the sensitive detection of specific mRNA. The method can occur as follows: cell lysates are applied to a substrate onto which oligo d(T) are immobilized, thus collecting cellular mRNA (for example, the Geneplate® manufactured by RNature). After the specific mRNA is captured, un-hybridized materials are removed by aspiration. Then, the captured mRNA is hybridized with a fluorescently labeled specific oligonucleotide probe(s). Unhybridized oligonucleotide probe(s) are removed by washing. The mRNA is then dissociated from the poly(A) by adding hot water, and transferred to the SCP where concentrated electrophoresis buffer was previously placed. Because the fluorescent molecules are packed into a small spot (the sample collector) during electrophoresis, detection sensitivity is enhanced.

For immunological detection (proteins, viral molecules, antibodies, small compounds, etc.), samples are placed into a microplate where specific antibodies are immobilized. After the biomolecules recognized by the specific antibodies are captured, non-specific materials are removed by aspiration. Then a fluorescently labeled secondary antibody is applied. After the unbound secondary antibodies are removed, the specifically bound labeled secondary antibodies are removed from the plate by adding acid, base, excess antigens, etc., and transferred to a SCP. If an appropriate buffer is used, and electrophoresis is started in the proper direction, fluorescently labeled antibodies will be concentrated in the spot (sample collector) at the bottom of the SCP and concentrated enough for sensitive detection.

If test samples contain a target molecule only in a very dilute form, fluorescent probes may not be essential.

This is because the electric current decreases during electrophoresis because of the increase in electric resistance due to the accumulation of materials onto the dialysis membrane. By measuring the slope of the decrease in electric current, the concentration of the target can be calculated.

If test samples are reacted with multiple probes with different colored markers attached, multiple biomolecules can be determined simultaneously.

Furthermore, by using dialysis membranes with appropriate pore sizes the washing step to remove un-reacted probes may be eliminated. For example, if fluorescently labeled oligonucleotide probes are 20-mers (approximately 6000 daltons in molecular weight), and the pore size of the dialysis membrane is >10,000, the un-reacted probes will pass through the dialysis membrane, whereas hybridized probes will stay on the top of dialysis membrane because of the larger size of the complex with mRNA.

The assay using the method and/or apparatus disclosed herein is rapid and sensitive, and does not require enzymatic amplification. Moreover, the electrophoresis microspot concentration apparatus (EMC) can accept diluted samples with a large volume which can then be concentrated into a very small volume. The method and/or apparatus may be used to analyze the concentration of biomolecules by continuously monitoring fluorescent signals during electrophoresis. In this way, the amounts of target biomolecules can be quantitated by the slope of the fluorescence increase before the signal plateaus (an end point assay).

The concentrated materials may be used for detection, analysis of concentration, and for recovery of the biomolecule for use in subsequent applications. For example, the sample may be used for applications including but not restricted to: sequencing, cloning, amino acid analysis, and as a probe.

One of the most important features of EMC is that all three components of the assay (the UEP, SCP, and LEP) are suitable for mass production or high throughput applications.

This assay provides a number of advantages over methods used previously. The method is rapid and sensitive, and does not require enzymatic amplification making it more affordable. In addition, the amounts of target biomolecules can be quantitated.

Subsequent Electrophoretic Characterization

Figure 6B:
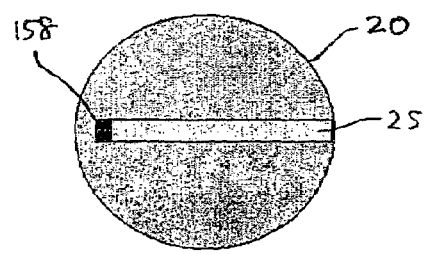
FIG. 6B is a top view prior to electrophoresis.

In order to further characterize concentrated biomolecules, a different embodiment can be developed using a sample concentration plate (SCP) 20. As shown in FIG. 6B, a sample collector (a tiny opening) 158 is placed on the left side of the SCP 20, and an open top electrophoresis microchannel 45 is attached. Before applying a sample containing a biomolecule, a viscous linear gel (such as hydroxymethyl cellulose) 25 is applied to the SCP, and centrifuged. Underneath the sample collector, a tiny hole is formed which is covered with a membrane such as a dialysis membrane so that the first buffer and the second buffer can be brought in electrical contact with each other, and the gel can stay in the channel. In this way, the microchannel is filled with a linear gel. As for the microchannel, a microchannel chip such as a DNA chip can be used. With regard to DNA chips, the disclosure of U.S. Pat. No. 6,251,247, issued Jun. 26, 2001 (application Ser. No. 09/281,385) is herein incorporated by reference in its entirety. An embodiment of the DNA chips disclosed in the patent has two channels for introduction of a sample and for detection, respectively. The microchannel usable here needs only one channel for electrophoresis.

Figure 5A:
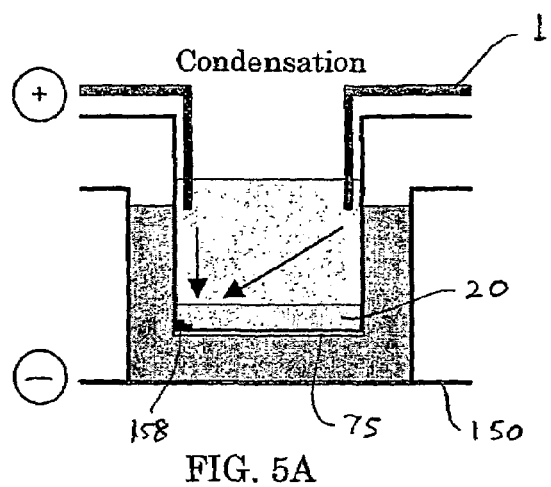
FIG. 5A is a schematic diagram showing an electrophoretic microspot concentration apparatus for electrophoretic characterization according to an embodiment of the present invention.
Figure 5B:
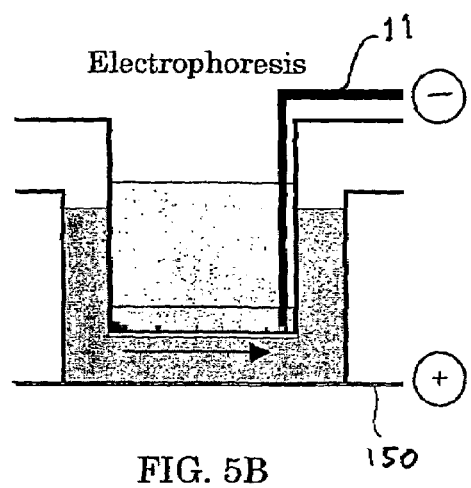
FIG. 5B is a schematic diagram showing the process of electrophoretic characterization subsequent to the electrophoretic microspot concentration shown in FIG. 5A.
Figure 6C:
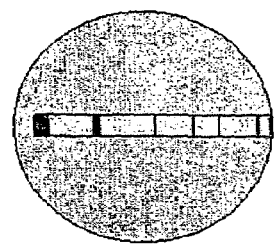
FIG. 6C is a top view after electrophoresis.
Figure 6A:
FIGS. 6Aa, 6B, and 6C are schematic diagrams showing a bottom portion used in the apparatus of FIGS. 5A and 5B, wherein a channel containing a linear gel for electrophoresis is formed.

The biomolecule sample is then carefully overlayed onto the top of the linear gel 25, and electrophoresis is performed until the sample is concentrated at the sample collector 158 (FIG. 5A). Once the biomolecules are concentrated on the dialysis membrane 75, the upper electrode 1 is changed to a long pin 11 (FIG. 5B), and the second electrophoresis is started with the electrodes in the reverse orientation (the lower electrode 150 is changed from the cathode to the anode). In this way, the sample is electrophoretically separated into multiple components (FIG. 5B). FIGS. 6A-6C show the linear gel embodiment in which the gel is inset into the sample container bottom (FIG. 6A). The concentrated sample (FIG. 6B) is subjected to electrophoresis upon reversal of the electrodes and the sample is separated (FIG. 6C).

Recently commercialized microchannel electrophoresis chips are restricted to only accepting small volumes of samples (the cross section between the injection channel and the separation channel is usually at the nL level). In contrast, the technology disclosed herein can start with a large dilute volume of sample even at the mL level. In addition, because the sample is concentrated into the microspot within the separation microchannel, the injection channel is completely eliminated. This reduces or eliminates sample loss.

EXAMPLES

In the following examples, the method and apparatus were tested for use in concentration, quantitation, and analysis of biomolecules. Initially, a loading dye was used to test the act of concentrating dilute samples into the sample collector using the EMC apparatus and the method of the preferred embodiment (see Example 1).

Example 1

Electrophoretic Concentration of a Loading Dye 10 1 of loading buffer (orange G, Xylene Cyanol, and Bromophenol blue) was applied to the sample container in 3 mL of buffer. A voltage and current were applied as shown and electrolysis was analyzed after 5, 10 and 30 minutes. The results are shown in Table 1. In all cases the Anode buffer or electrophoresis buffer used was 1×TBE. EO refers to elution of the Orange G from the dialysis membrane, EB refers to elution of the Bromophenol blue from the dialysis membrane, and EX refers to elution of the xylene cyanol from the dialysis membrane.

TABLE 1

The results of electrophoresis of a loading dye under various conditions.

| Cathode buffer + 10 microl load dye in 3 mL buffer | Applied Voltage (current) | Electrolysis After 5 min | Electrolysis After 10 min | Electrolysis After 30 min | comments |
|---|---|---|---|---|---|
| 10 mM Tris, 1 mM EDTA | 150 V(9 mA) | EO | | EB | Air generation |
| 10 mM Tris, 10 mM EDTA | 150 V(30 mA) 93 V(10-15 mA) 1 min | EO | | EB (15 min) | Air generation |
| 10 mM Tris, 10 mM EDTA | 34 V(4 mA) | + | 2+, EO | 2+, EB, | air generation: 16 min- |
| 10 mM Tris, 10 mM EDTA | 22 V(2 mA) | + | 2+ | 2+ EO, EB, EX | air generation: 38 min- |
| 10 mM Tris, 5 mM EDTA | 22 V(1 mA) | − | 2+ | 3+ | No air generation |
| 10 mM Tris, 50 mM EDTA | 22 V(3 mA) | − | − | + | No air generation |
| 1× TBE | 22 V(1 mA) 34 V(2 mA) 18 min- | − | + | EO | No air generation |
| 1× MOPS 10 mM EDTA | 22 V(3 mA) | + | + | | No air generation |

MA = milliAmps,
V = Volts,
(+) means that the dye was concentrated into the sample collector,
(−) means that no change was detected.
No air generation means no gas or bubles were produced, 2+ and 3+ refer to the degree of accumulation of the dye at the spot.

The results shown above show that the method and apparatus is useful for the concentration of a biomolecule. Various cathode buffers were tested for their efficacy and various voltages were applied. It was preferable to choose a buffer and voltage which did not contribute to air production. For example, due to gas generation, concentrated samples such as an oligonucleotide would be rediluted back into the bulk solution, reducing the efficiency and yield. Typically, the amount of dye which was concentrated improved after ten minutes and often after 20 minutes. Thus, in Example 2, the method and apparatus were next tested for the efficacy in concentrating a dilute oligonucleotide.

Example 2

Electrophoretic Concentration of Oligonucleotide

A test oligonucleotide (SEQ ID NO:1), a 53mer, was synthesized and diluted with cathode buffer. A fluorescent DNA dye was added and the sample containing the oligonucleotide was applied to the SCE to be concentrated. Experimental conditions were as follows:

The Cathode buffer was TE (10 mM Tris, 10 mM EDTA). Various concentrations of the Oligonucleotide plus a set concentration of the fluorescent dye, OliGreen were added and brought up to 3 mL with the TE buffer, thus producing a dilute sample.

The Anode buffer or electrophoresis buffer was 1×TBE and was degassed by aspiration prior to electrolysis.

After the Anode buffer was added to the second container and the dilute sample was added to the first container, the apparatus was set up and Electrolysis using a constant voltage of 22V (2-3 mA) was initiated.

The oligonucleotide used was a ssDNA 53mer with the sequence: 5'(C6-NH2) AGC TGA ATT CGC GGC CGC AAT ACG ACT CAC TAT AGT TTT TTT TTT TTT TTT TT3' (SEQ ID NO: 1)

The results are shown in Table 2. The concentration was analyzed by fluorescence of the OliGreen™ as follows:

TABLE 2

Fluorescence measured by plate reader (mean of duplicate samples)

| Electrolysis | 22.7 ug/mL ssDNA | 2.27 ug/mL ssDNA | 22.7 ng/mL ssDNA |
|---|---|---|---|
| 0 min | 2565 | 1281 | 40 |
| 5 min | 2364 | 1105 | 32 |
| 10 min | 2305 | 1088 | 31 |
| 20 min | 953 | 834 | 26 |
| 30 min | 156 | 770 | 30 |
| 40 min | | 430 | |
| 60 min | | | 19 (back ground) |

Figure 9A:
FIGS. 9A, 9B, and 9C are photographs showing electrophoretic concentration of 2.27 µg/ml oligonucleotides by electrolysis at 22 V at a time passage of 0 min (FIG. 9A), 10 min (FIG. 9B), and 30 min (FIG. 9C).
Figure 9B:
Figure 9C:

FIGS. 9A, B, and C show the progression of electrophoretic concentration of 2.27 μg/mL of the oligonucleotide by electrolysis at 22 V at 0 min (FIG. 9A), 10 min (FIG. 9B), and 30 min (FIG. 9C). It is clear that after 30 minutes most of the biomolecule in the form of the oligonucleotide bound by the fluorescent dye, oligreen was contained in the microspot.

Assuming that 1 μL of a 50 ng/μL sample of template DNA is commonly used for PCR, the above electrophoretic concentration method could provide as high a concentration of oligonucleotides as those used for PCR. Because of the fact that the fluorescence intensity decreased even at 22.7 ng/mL of ssDNA, it is likely that it is possible to detect the amount of template DNA necessary for PCR upon modifications of experimental conditions.

When concentrating biomolecules using the method and apparatus described in Examples 1 and 2, it is possible to lose sample or efficiency due to gas generation or bubbles on the dialysis membrane. Thus the methods in Example 3 were developed to avoid gas generation.

Example 3

Methods for Avoiding Gas Generation on Dialysis Membrane

The following methods were determined to avoid gas generation on the dialysis membrane. These methods include but are not restricted to: 1. controlling the applied potential and/or current 2. choosing the best composition of electrolyte and choosing the best conductivity of the electrolyte 3. Degassing the electrolyte before use (time of air generation changed from 30 min to 100 min by degassing) 4. Pretreating the dialysis membrane 5, boiling the membrane prior to attachment and 6. Applying approximately 100 volts for 5 min prior to electrolysis. Typically, the dialysis membranes were boiled and degassed under house vacuum overnight.

Example 4

Figures 4A, 4B:
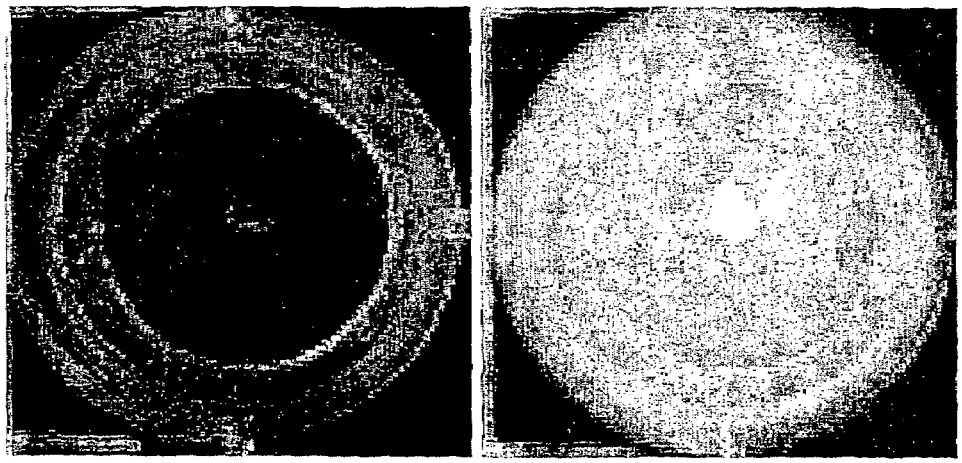
FIGS. 4A and 4B show electrophoresis of ethidium bromide stained rRNA.

Electrophoresis of Ethidium Bromide Stained rRNA 0.2 g of rRNA was suspended in TE in the presence of 0.5 μg/mL ethidium bromide (EtBr). The sample was applied to the SCP. The SCP was then inserted into the LEP, which contained TBE buffer. 100 volts were applied and approximately 10 mA were generated. After electrophoresis for 10 minutes, the plate was placed on a U.V. box and a polaroid picture was taken. FIGS. 4A and 4B show the results. In FIG. 4A, the small hole (microspot) is indicated in the center, and the microspot is covered with a dialysis membrane. After only 10-minute electrophoresis (FIG. 4B), the ethidium bromide stained rRNA was highly concentrated into the microspot onto the dialysis membrane.

Example 5

Electrophoretic Concentration of Xylene Cyanol

Figure 7:
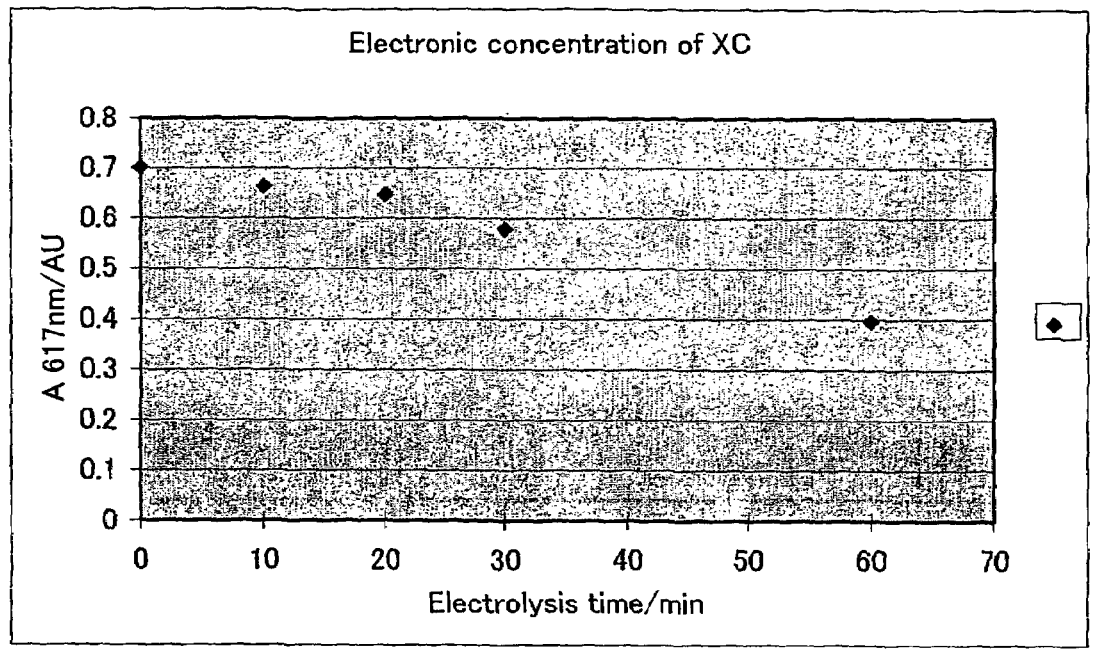
FIG. 7 is a graph showing the absorbance of various concentrations of a xylene cyanol sample as a function of time.
Figure 8:
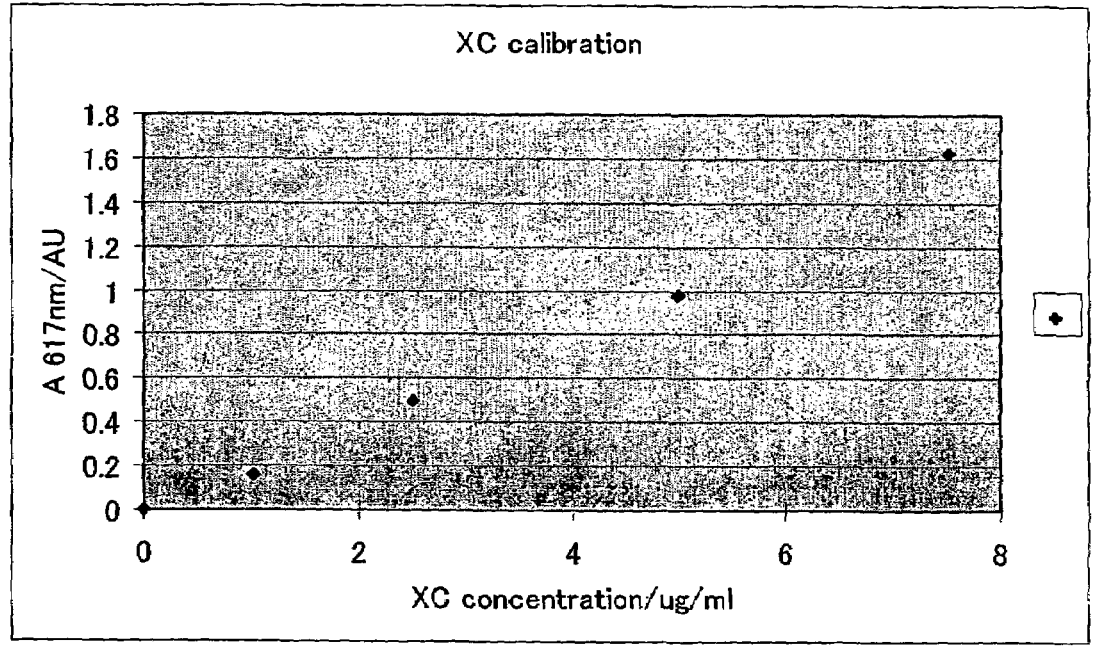
FIG. 8 is a graph showing the absorbance of various concentrations of xylene cyanol as a function of concentration.

Xylene cyanol (XC) was electrophoresed and the electrophoresis graphed as a function of time and concentration. The cathode buffer used was 10 mM Tris, 10 mM EDTA+ xylene cyanol (3.3 g/mL). The anode buffer was 1×TBE, The electrolysis was conducted at a constant voltage of 22V (2-3 mA). The concentration was analyzed at 10 minutes, 30 minutes, 60 minutes and 80 minutes at A617 nm/AU. FIG. 7 shows that the Electronic concentration of XC in the sample buffer decreased from 3.3 g/mL to 1.9 g/mL over approximately 80 minutes. FIG. 8 shows the XC calibration of A617 nm/AU graphed as a function of XC concentration (g/mL). The maximum absorbance of xylene cyanol was at 617 nm. The above results suggest that xylene xyanol may be used an indicator that the electrophoresis is going well. Particularly if the analysis of the sample will be by fluorescence or radioactivity.

Example 6

A Method for the Identification and Analysis of Virus in a Sample

The concentration of HIV in cerebrospinal fluid (CSF) is determined as follows: CSF from a patient is diluted with buffer. Prior to dilution or after, fluorescently labeled antibodies specific for HIV are added to the CSF sample and allowed to react. The sample is applied to the container in the SCP, and electrophoresed. Fluorescence is monitored in the sample collector. If no fluorescence is detected, the patient is diagnosed as not having HIV meningitis. In the above, because viruses are much bigger than antibodies, unrecalled antibodies may pass through the membrane so that unrecalled labeled antibodies may not interfere with detection of viruses reacted with labeled antibodies.

Example 7

A Method for the Analysis of the Efficacy of Gene Therapy

The concentration of protein expressed by recombinant adenovirus in a sputum sample from a patient with Cystic Fibrosis is determined as follows: The sample is diluted with buffer. Before or after dilution, a fluorescently labeled antibody probe specific to the recombinant protein expressed by the recombinant adenovirus is added to the sample and allowed to bind. The protein reacted with the probe is captured in a solid phase of an affinity column, and stained with labeled second antibody probe. After washing, an elute is recovered to obtain a sample including the protein. The sample is applied to the container in the SCP, electrophoresed, and fluorescence is analyzed as a matter of time of electrophoresis. The florescence is graphed as a function of time. The concentration is determined by analyzing the slope of the graph prior to a plateauing of the fluorescence signal. In this way, the amount of recombinant protein for the treatment of the Cystic Fibrosis is assessed and treatment monitored.

Example 8

Identification of the Presence of a Transcript within a Cellular Sample

The expression of Interferon gamma is monitored in a blood sample from a patient with ebola as follows: The total RNA is isolated from the blood cells and bound to a GENEPLATE (from RNature, Irvine Calif.) The mRNA binds to the GENEPLATE and the rest of the sample is aspirated. cDNA is then produced from the mRNA and the cDNA is transferred to the SCP in an appropriate buffer. A radioactively labeled probe specific for the interferon gamma gene is added and allowed to react before or after addition of the sample to the SCP. The dialysis membrane is chosen to retain probe which has bound the cDNA, while unbound probe goes through. The sample is then electrophoresed and the amount of radioactivity retained in the sample collector is quantitated.

Example 9

Identification of the Presence and Concentration of a Protein Using Antibodies Specific to that Protein Studies have identified the presence of elevated serum alpha-fetoprotein in adults as an indicator of various disease states including cancer, particularly liver cancer, and other liver disease. Thus, the serum from an adult patient is isolated and a fluorescent antibody specific to alpha-fetoprotein is added in conditions which are conductive to the binding of antibody to antigen. The sample is subjected to microspot concentration using a dialysis membrane which retains alpha-fetoprotein-antibody conjugates, but allows unbound antibody to go through the pores. The amount of fluorescence is determined and compared to a normal control. Those patients with increased amounts of alpha-fetoprotein undergo a thorough evaluation to rule out malignant disease.

Example 10

Concentration and Analysis of Affinity Bound Proteins Using the Microspot Concentration Coupled to a Linear Polyacrylamide Gel An affinity column is produced by covalently bonding an oligonucleotide to a cyanogen bromide coupled matrix.

The oligonucleotide corresponds to a segment of the Varicella Zoster virus LTR (long terminal repeat), a viral promoter. Of interest is the identification of a factor within human cells which binds to the viral promoter and exerts repression or activation of expression of the viral proteins. Thus, cell extracts from nerve cells are applied to the LTR affinity column. Any proteins within the cells which specifically bind to the viral promoter sequence are allowed to bind and then the column is washed. Bound proteins are eluted and the eluant is added to the microspot concentrator as in Example 1. After concentration, the electrodes are switched to the reverse orientation and the proteins are run on a linear polyacrylamide gel to allow separation, MW analysis, and purification. The purified proteins are then sequenced.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. An apparatus for the concentration of biomolecules in a sample, comprising:
    a first compartment for containing a first buffer to which a sample containing biomolecules is added;
    a second compartment for containing a second buffer including no sample;
    an insulation wall separating the first compartment and the second compartment, said insulation wall having a fine throughhole;
    a membrane covering the throughhole and blocking biomolecules contained in the sample from passing therethrough, wherein the first buffer and the second buffer are insulated by the insulation wall except for the throughhole covered with the membrane when the sample is loaded, wherein the first buffer and the second buffer are in electrical contact with each other via the membrane;
    a first electrode provided in the first compartment to contact the first buffer when loaded;
    a second electrode provide in the second compartment to contact the second buffer when loaded, wherein when a voltage is applied between the first and the second electrodes, biomolecules in the sample are subjected to electrophoresis and concentrated at the membrane-covered throughhole; and
    an outer container in which the second compartment is formed, wherein said outer container has a bottom which constitutes the second electrode.

2. An apparatus for the concentration of biomolecules in a sample, comprising:
    a first compartment for containing a first buffer to which a sample containing biomolecules is added;
    a second compartment for containing a second buffer including no sample;
    an insulation wall separating the first compartment and the second compartment, said insulation wall having a fine tbroughhole, wherein the isolation wall is formed in a container having a top opening and a bottom having the throughhole, wherein the first compartment is provided inside the container, and the second compartment is provided outside the container;
    a membrane covering the tbrougbhole and blocking biomolecules contained in the sample from passing therethroug, wherein the first buffer and the second buffer are insulated by the insulation wall except for the throughhole covered with the membrane when the

---

SEQUENCE LISTING

<160> NUMBER OF SEQ ID NOS: 1

<210> SEQ ID NO 1
<211> LENGTH: 53
<212> TYPE: DNA
<213> ORGANISM: Artificial Sequence
<220> FEATURE:
<223> OTHER INFORMATION: Test Oligonucleotide

<400> SEQUENCE: 1
agctgaattc gcggccgcaa tacgactcac tatagttttt ttttttttt ttt      53 sample is loaded, wherein the first buffer and the second buffer are in electrical contact with each other via the membrane;
a first electrode provided in the first compartment to contact the first buffer when loaded; and
a second electrode provide in the second compartment to contact the second buffer when loaded, wherein when a voltage is applied between the first and the second electrodes, biomolecules in the sample are subjected to electrophoresis and concentrated at the membrane-covered throughhole;
wherein the membrane is attached to the bottom of the inner container by heat sealing, adhesives, or sonication.

3. An apparatus for the concentration of biomolecules in a sample, comprising;
a plurality of containers comprising a first compartment for containing a first buffer to which a sample containing biomolecules is added, and a second compartment for containing a second buffer including no sample;
an insulation wall in each of said containers separating the first compartment and the second compartment, said insulation wall having a fine througbhole, wherein the isolation wall is formed in a container having a top opening and a bottom having the througbhole, wherein the first compartment is provided inside the container, and the second compartment is provided outside the container;
a membrane covering each throughhole and blocking biomolecules contained in the sample from passing therethrough, wherein the first buffer and the second buffer are insulated by the insulation wall except for the throughhole covered with the membrane when the sample is loaded, wherein the first buffer and the second buffer are in electrical contact with each other via the membrane;
a first electrode provided in the first compartment to contact the first buffer when loaded;
a second electrode provide in the second compartment to contact the second buffer when loaded, wherein when a voltage is applied between the first and the second electrodes, biomolecules in the sample are subjected to electrophoresis and concentrated at the membrane-covered throughhole; and
a plurality of outer containers in which the second compartment is formed, wherein the containers are used as inner containers and fitted in the respective outer containers, wherein said inner and outer containers are made of plastic and formed by injection molding and wherein each outer container has a bottom which constitutes the second electrode.

4. An apparatus for the concentration and detection of biomolecules in a sample, comprising:
a first compartment for containing a first buffer to which a sample containing biomolecules is added;
a second compartment for containing a second buffer including no sample;
an insulation wall separating the first compartment and the second compartment, said insulation wall having a channel filled with a gel for electrophoresis, said channel covered with an insulation sheet except for one end spot of the channel, said insulation wall having a hole underneath the end spot, said hole being covered with a membrane, wherein when the sample is loaded, the first buffer and the second buffer are insulated by the insulation wall except for a place where the end spot and the hole are located and the gel is present therebetween, wherein the first buffer and the second buffer are in electrical contact with each other via the gel;
a first electrode provided in the first compartment to contact the first buffer when loaded;
a second electrode provide in the second compartment to contact the second buffer when loaded, wherein when a voltage is applied between the first and the second electrodes, biomolecules in the sample are subjected to electrophoresis and concentrated at the end spot; and
a third electrode provided at another end of the channel opposite to the end spot, wherein a voltage is applied between the second electrode and the third electrode, biomolecules concentrated at the end spot are subjected to electrophoresis along the channel toward the third electrode.

5. The apparatus of claim 4, wherein said gel is a linear gel.

6. The apparatus of claim 5, wherein said outer container has a bottom which constitutes the second electrode.

7. The apparatus of claim 4, wherein the isolation wall is shaped in a container having a top opening and a bottom plate having the channel, wherein the first compartment is provided inside the container, and the second compartment is provided outside the container.

8. The apparatus of claim 7, wherein said first electrode is formed in a shape fitted inside the container.

9. The apparatus of claim 7, further comprising an outer container in which the second compartment is formed.

10. The apparatus of claim 4, further comprising an outer container in which the second compartment is formed.

11. A method for the concentration of biomolecules in a sample, comprising:
applying a sample to a first buffer, said first buffer being separated from a second buffer by an insulation wall having a fine throughhole, wherein a membrane covers the throughhole, said membrane being capable of blocking biomolecules contained in the sample from passing therethrough, wherein the first buffer and the second buffer are insulated by the insulation wall except for the tbroughhole covered with the membrane via which the first buffer and the second buffer are in electrical contact with each other;
imposing a voltage difference between the first and the second buffers to subject biomolecules in the sample to electrophoresis, thereby concentrating the biomolecules at the membrane-covered throughhole; and
detecting the concentrated biomolecules, wherein said biomolecule is reacted with a detection moiety before concentration, wherein said detection moiety is a substance which passes through the membrane.

12. A method for the concentration of biomolecules in a sample, comprising:
applying a sample to a first buffer, said first buffer being separated from a second buffer by an insulation wall having a fine throughhole, wherein a membrane covers the throughhole, said membrane being capable of blocking biomolecules contained in the sample from passing therethrough, wherein the first buffer and the second buffer are insulated by the insulation wall except for the throughhole covered with the membrane via which the first buffer and the second buffer are in electrical contact with each other;
imposing a voltage difference between the first and the second buffers to subject biomolecules in the sample to electrophoresis, thereby concentrating the biomolecules at the membrane-covered throughhole; and detecting the concentrated biomolecules by measuring a slope of a decrease in electric current between the first and second electrodes during electrophoresis.

13. A method for the concentration of biomolecules in a sample, comprising:
applying a sample to a first buffer, said first buffer being separated from a second buffer by an insulation wall having a fine throughhole, wherein a membrane covers the throughhole, said membrane being capable of blocking biomolecules contained in the sample from passing theretbrough, wherein the first buffer and the second buffer are insulated by the insulation wall except for the tbrougbhole covered with the membrane via which the first buffer and the second buffer are in electrical contact with each other;
imposing a voltage difference between the first and the second buffers to subject biomolecules in the sample to electrophoresis, thereby concentrating the biomolecules at the membrane-covered througbhole; and
of quantifying biomolecules by monitoring the accumulation of biomolecules over a period of time; graphing the data; and determining the slope before the signal plateaus.

14. The method of claim 13, wherein the quantitation of biomolecules is conducted by measuring a slope of an increase in signals from detection moieties reacted with the biomolecules before concentration.

15. The method of claim 13, wherein the quantitation of biomolecules is conducted by measuring a slope of a decrease in electric current between the first and second electrodes during electrophoresis.

16. A method for the concentration and detection of a biomolecule in a sample, comprising:
applying a sample to a first buffer, said first buffer being separated from a second buffer by an insulation wall having a channel filled with a gel for electrophoresis, said channel covered with an insulation sheet except for one end spot of the channel, said insulation wall having a hole underneath the end spot, said hole being covered with a membrane, wherein the first buffer and the second buffer are insulated by the insulation wall except for a place where the end spot and the hole are located and the gel is present therebetween, wherein the first buffer and the second buffer are in electrical contact with each other via the gel;
imposing a voltage difference between the first and the second buffers to subject biomolecules in the sample to electrophoresis, thereby concentrating the biomolecules at the end spot; and
imposing a voltage difference between another end of the channel opposite to the end spot and the second buffer to subject the biomolecules concentrated at the end spot to electrophoresis along the channel toward the other end of the channel.

17. The method of claim 16, wherein said biomolecule is selected from the group consisting of: DNA, rRNA, mRNA, tRNA, oligonucleotides, proteins, peptides, small molecules, lipids, steroids, microbes, and viruses.

18. The method of claim 17, further comprising detecting the concentrated biomolecules at the end spot, wherein said biomolecule is reacted with a detection moiety before concentration.

19. The method of claim 18, wherein said detection moiety is selected from the group consisting of: a fluorescent dye, a fluorescent antibody, a fluorescent oligonucleotide, a colored marker, a dye, a radioactive label, and an intercalating agent.

* * * * *